United States Patent [19]
Davis

[11] Patent Number: 5,213,569
[45] Date of Patent: May 25, 1993

[54] TIP FOR A TISSUE PHACOEMULSIFICATION DEVICE

[76] Inventor: Peter L. Davis, 7688 Tronson Road, Vernon, British Columbia, R.R. #4, Canada

[21] Appl. No.: 861,016
[22] Filed: Mar. 31, 1992
[51] Int. Cl.⁵ .............................. A61B 17/20
[52] U.S. Cl. ........................ 604/22; 604/294; 606/107; 606/161
[58] Field of Search ............ 606/107, 161, 166, 171, 606/223; 604/21, 22, 46, 239, 272-274, 264, 268, 294

[56] References Cited

U.S. PATENT DOCUMENTS

| | | | |
|---|---|---|---|
| 3,990,452 | 11/1976 | Murry et al. | 128/24 AA |
| 4,531,934 | 7/1985 | Kossovsky et al. | 604/22 |
| 4,689,040 | 8/1987 | Thompson | 604/22 |
| 4,816,018 | 3/1989 | Parisi | 128/24 AA |
| 4,838,853 | 6/1989 | Parisi | 604/22 |
| 5,092,837 | 3/1992 | Ritch et al. | 604/294 |
| 5,112,339 | 5/1992 | Zelman | 606/161 |

Primary Examiner—Stephen C. Pellegrino
Assistant Examiner—Jeffrey A. Schmidt
Attorney, Agent, or Firm—William L. Klima

[57] ABSTRACT

Phacoemulsification needles having distal ends with focusing surfaces for concentrating ultrasonic generated acoustic waves. The focusing surfaces can be beveled and/or provided with continuous curved or faceted surfaces.

41 Claims, 1 Drawing Sheet

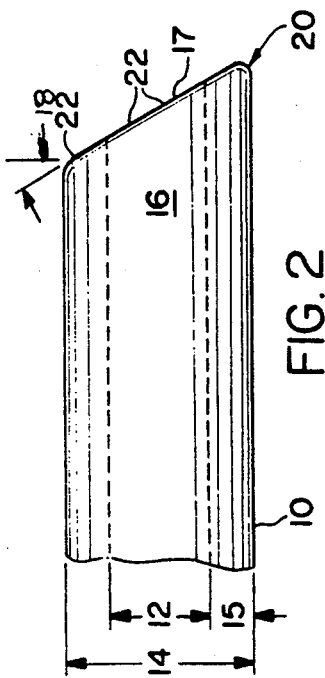
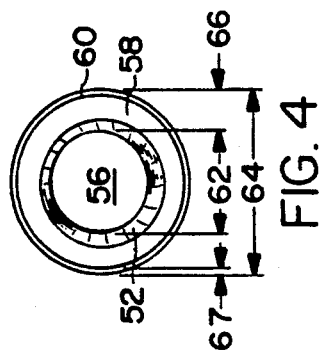
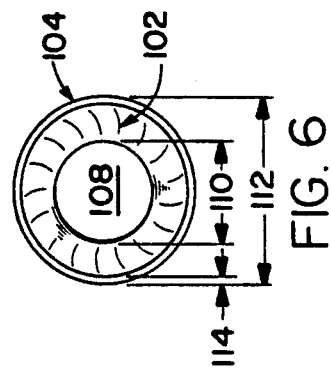
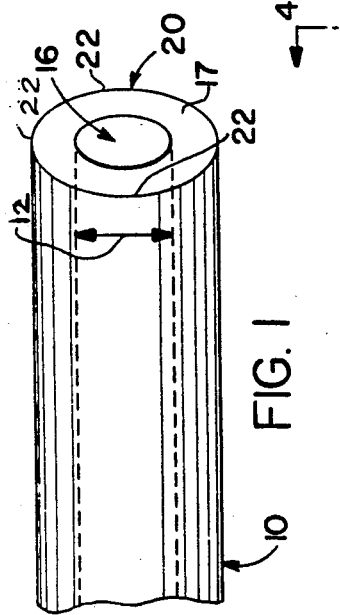
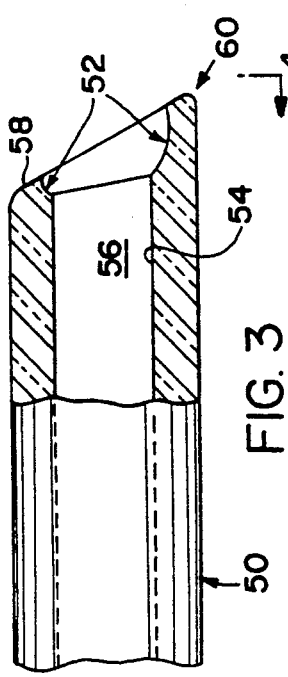
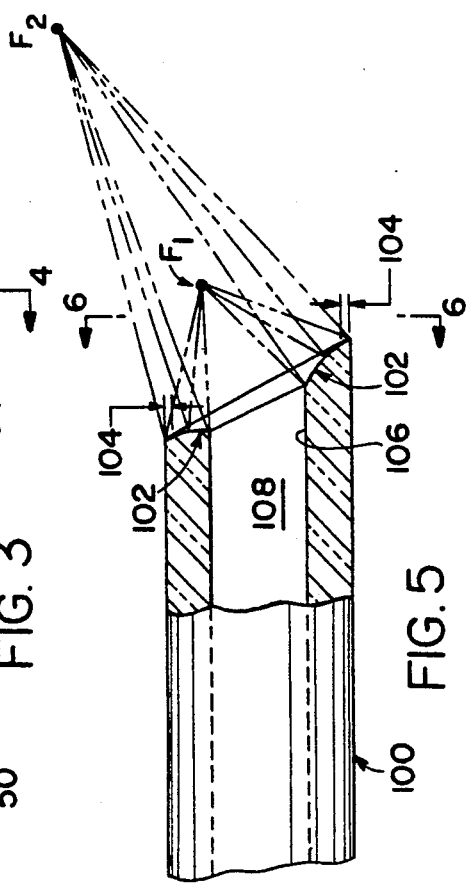

TIP FOR A TISSUE PHACOEMULSIFICATION DEVICE

BACKGROUND OF THE INVENTION

1. Field of the Invention

This invention relates to surgical instruments, more particularly to improved tips for phacoemulsification needles ultrasonically energized by phacoemulsification surgical devices.

2. Prior Art

Phacoemulsification (PHACO) surgical instruments are used for the erosion and pulverization of malfunctioning or diseased tissue of the eye, in particular the opaque hardened protein of cataract of the eye. Electrical energy is delivered to an acoustic wave generating hand held transducer that conducts energy into the eye via a thin walled (e.g. 0.050 millimeter) tip. The tips available are hollow and generally have a 1.0 millimeter (mm) outside diameter, 0.90 to 0.91 mm internal diameter. These tips are made of titanium metal and have a beveled end. The end faces of the tips were originally set at a 15 degree angle, but are currently available set at 30 to 45 degree angles. In addition, the tips have been made with thinner walls and oval cross sections to allow easier entry into the eye.

Balanced salt solution is delivered by gravity infusion into the eye via an infusion tube and a silicone sleeve that surrounds the tip. A hydraulic pump aspirates the pulverized material which is carried along by the salt solution out of the eye via the hollow center lumen of the titanium tip.

These surgical instruments have consoles that provide an aspirating pump that removes balanced salt solution from the operative site and carries with it the eroded tissue. These consoles also deliver electrical energy to the transducer hand piece that converts electrical to acoustic ultrasonic energy. A piezoelectric crystal generates vibrations in the 28,00 to 50,000 cycles per second range and these vibrations are transmitted to a threaded on titanium hollow metal tip 24 mm in length and 1.0 mm in width. New designs for such titanium tips have only appeared recently.

A non-vibrating plastic sleeve surrounds the tip, and salt solution is delivered by gravity to the anterior chamber of the eye into which the phacoemulsification tip with its encasing plastic sleeve have been inserted. As acoustic energy is delivered to the tip nearby tissue is eroded, and the aspirating pump then removes the tissue fragments along with a portion of the salt solution.

It is desirable to erode the hard cataract material within the thin transparent capsule that surrounds the lens of the eye to prevent injury to other tissues in the area such as corneal endothelium and iris. To accomplish this, a precise delivery of energy must be delivered by the vibrating metal tip. Sharp edges on the tip can inadvertently tear the capsule or cornea, and allow vitreous gel located deeper in the eye to move forward. This often impairs effective healing and prevents satisfactory visual recovery.

The procedure of using ultrasonic acoustic wave field erosion of the nucleus of the lens of the human eye is being utilized more frequently. Typically, a hand held transducer of the type described above is used in these procedures. The hand held transducer converts alternating electrical current into acoustic waves, and is a complex and powerful device. The basic mechanism for this energy conversion is well understood by electrical engineers and physicists.

In spite of this understanding by electrical engineers and physicists, and the large industrial use of ultrasound in chemical and material processing, clinical medicine, and cleaning procedures, there has been almost a complete lack of review materials on the underlying principles from which ultrasonic effect originates. This observation is especially true concerning how ultrasound works within the human eye.

Designed in the 1960's by the Cavitron Corporation in association with Charles Kelman, M.D. of New York City, the erosion mechanism is generally believed to be a mechanical "jack hammer" cutting action by the soda straw-like metal tube having an oblique end, and being ultrasonically vibrated. More specifically, the sharp titanium tip is ultrasonically vibrated and acts as a sort of hollow jack hammer that cuts into and mechanically disrupts the cataract nucleus. This approach has lead to the development of tips having sharp edges and thin walls to better "cut" the cataract. This "jack hammer" concept is the prevailing view of how the phaco device erodes or emulsifies tissue.

In these prior art tips, there exists no structure, or means for focusing the acoustic wave front. Specifically, the thin wall of one of these tips terminates to a small circular end face or rim of approximately 0.050 to 0.1 mm in thickness, the end face being set obliquely to the longitudinal axis of the tip. The geometry of this tip is defined by a flat planar surface of the end face intercepting the cylindrical outside surface of the tip.

This surface geometry does not focus wave energy, but only generates waves normal to the flat planar surface of the end face and diverging waves from the outer cylindrical surface of the tip. Thus, these prior art tips may require to some extent actual contact with the tissue to carry out the "jackhammer" effect. Accordingly, these prior art devices are manufactured with shape edges to more effectively cut tissue. Further, sharpened tips suggest and have resulted in the present thin walled structured tips to increase the penetrating ability of the leading edges of these tips, similar in concept to needle designs for puncturing skin tissue.

Acoustic wave energy physics research done since the 1960's reveals possibilities of other mechanisms for tissue erosion with improved tip designs. Upon careful evaluation of the acoustic energy literature, it is now believed that even the prior art tips do not have to actually touch the cataract nucleus during phacoemulsification to effectively remove tissue. Instead, the energy that erodes the nucleus is created by clouds of millions of acoustic wave generated 80–150 micron sized bubbles by the surfaces of the tip being ultrasonically vibrated. The micron sized bubbles are generated at the end of the metal rim (acoustic horn), and expand and implode within a few acoustic cycles creating massive shock waves (500 atmospheres) plus fluid waves at 400 km/hr.

These micro bubbles have been photographed by B. Svensson of Sweden in a plexiglas chamber, and these photos have been shown at the meeting of the American Society of Cataract and Refractive Surgery held in Boston, Mass. in April 1991. At that meeting, a paper also documented sonoluminescent (flame) activity at the tip of phaco devices. This phenomenon has also been photographed in the past and is well illustrated in the ultrasound acoustic literature. These imploding microbubbles, called "transient cavitation" in the physics literature, generate the energy that erodes any solid surface in the area when an acoustic cloud is released into fluid.

Phaco transducers cause the hollow titanium acoustic focusing horn to move back and forth approximately three (3) microns at a frequency selected by the designer believed to be most efficient for cataract nucleus pulverization. The most efficient types of phaco transducers generate acoustic fields primarily at the phaco tip with little loss laterally. This acoustic energy wave generates within a few cycles (in liquids) the bubbles of gas approximately 150 microns in size. These bubbles release large amounts of energy when they implode at the speed of sound and the process is known as "transient cavitation." These unstable microbubbles implode toward any solid surface in the area. The implosion generates shock waves of approximately 500 atmospheres (1 atm=14.9 lb/sq. in.), and fluid waves of 400 km/hr, plus temperatures of 5,500 Celsius within the bubble, especially if the sonicated fluid contains hydrocarbons.

A second form of cavitation is called "stable", implying some micron sized bubbles that last hundreds or thousands of acoustic cycles. Their activity is less well understood by researchers. The massive energy released by cavitation erodes the transducer tip necessitating that they be made of a metal such as titanium.

Even though surgical procedures involving the use of phacoemulsification surgical instruments having proven effective, there is some risk of phaco thermal injury to the anterior segment of the eye during the procedure. The implosion of microbubbles during the process generate massive fluid and shock waves that erode the solid material cataractous nuclei, and can release excess thermal energy into the eye. Further, residual heat from the phaco transducer is conducted down the hollow titanium needle (acoustic focusing horn) and radiates in the anterior chamber potentially causing thermal damage within the anterior segment. Piezoelectric transducers are more efficient and conduct less heat along the needle compared to older magnetostrictive type transducers.

To prevent heat damage, a constant flow of balanced salt solution in and out of the anterior segment is needed to transfer heat out of the eye and to remove lens debris (lens milk) so that the surgeon can visualize the area. However, any problem with proper balanced salt solution circulation can quickly result in heat damage to eye tissue. To insure proper circulation, it is recommended that the surgeon should personally:

1. Visually be certain that balanced salt solution (bss) is being aspirated from the transparent test chamber into the catchment device, that the test chamber remains filled or only slightly dimpled when the device is in phaco mode and held a eye level, and that bss exits from the silicone infusion ports before the device is placed in the anterior chamber;

2. Kink the infusion line while in phaco mode and watch for the test chamber to collapse. Follow this by kinking the aspiration line and listen for the sound of vacuum build up;

3. Ascertain that the incision is large enough for the phaco transducer tip being used, thus avoiding pinching the silicone infusion sleeve, and that some bss leaks from the incision;

4. Aspirate some viscoelastic, if present, from the anterior chamber before entering phaco mode to guarantee that balanced salt circulation not be impaired;

5. Avoid overtorquing the incision (greater tendency if made in the cornea) such that the silicone sleeve is compressed against the edges of the incision;

6. Be aware prolonged time in phaco mode delivers more heat via the titanium tip (use short bursts of phaco power during carving of the nucleus and consider use of pulse mode if available;

7. Become aware of venting sounds that many machines emit if aspiration is impaired; and 8. Watch for persistence of "lens milk", a whitish material of lens fragments in the area of the phaco tip, suggesting movement of bss is restricted. Rigid titanium infusion sleeves have been promoted to guarantee bss is infusing readily and that bss can leak from the incision. However, if these are malaligned they may be frayed by the phaco tip oscillations releasing metal fragments into the eye. The best prevention of thermal injury is to be aware that all transducers lose some energy as heat that is conducted via the titanium tip and that circulation of bss is essential to prevent thermal injury.

Other means for reducing the risk of heat damage can be provided by designing transducers with thermal sensors that stop the device if overheating occurs. Balanced salt solution is currently being chilled prior to its use during the phaco procedure. It could be circulated through larger channels in the transducer handle to create more cooling. It has been traditional for the acoustic horn titanium tip to have a thin wall with the tip bevelled between 15-45 degrees with a 0.91 mm lumen. This design has been used since the 1960's, and could be redesigned to create more efficient acoustic wave fields at the tip, thus eroding the nucleus with less energy, thereby reducing the risk of thermal and or chemical injury.

Researchers are studying the effects the enormous heat generated within liquids can have in forming new chemicals (sonochemistry). The phenomenon of the flame generated within the bubble is known as sonoluminence. This heat is rapidly dissipated and does not significantly contribute to raising the temperature of the liquid being sonicated. Sonochemists are aware that water is broken down to $H_2O_2$ and free OH radicals in ultrasonic acoustic fields generated by transducers with designs similar to those used in ophthalmic surgery. It has been demonstrated that these reactions are occurring in the eye during phacoemulsification (See Svensson, Eur. Soc. Cataract and Retract. Surg., September 1991).

SUMMARY OF THE INVENTION

An object of the present invention is to provide improved phacoemulsification tips.

Another object of the present invention is to provide phacoemulsification tips having means to increase the generation of micro bubbles formed by the tips during operation.

A further object of the present invention is to provide phacoemulsification tips that have rounded edges to prevent eye tissue damage.

A still further object of the present invention is to provide phacoemulsification tips having increased surface area at the distal ends thereof to increase the generation of micro bubbles formed by the tips during operation.

Another object of the present invention is to provide phacoemulsification tips having increased surface area end faces to increase the generation of micro bubbles formed by the tips during operation.

A further object of the present invention is to provide phacoemulsification tips that have surface geometry and structure for focusing ultrasonic generated acoustic waves.

A still further object of the present invention is to provide phacoemulsification tips that are resistant to wear and damage.

The phacoemulsification tips according to the present invention were developed to more efficiently erode eye tissue at lower energy levels than the existing devices. The lower energy level operation will reduce the risk of thermal damage to the eye. Further, the tips according to the present invention more effectively remove tissue without disrupting surrounding tissues and fluids and increase the speed of removal. Thus, the tips greatly improve the safety and reduce the time with respect to current surgical procedures.

The phacoemulsification tips according to the present invention takes advantage of a new approach to applying ultrasonic techniques. Instead of mechanically attempting to cut away eye tissue, these tips were developed to 1) increase the generation of micro bubbles, and/or 2) focusing the ultrasonic acoustic and shock waves, which effectively erode tissue in situ. For example, the tip is provided with curvature means extending around a perimeter having a configuration for increasing the generation of microbubbles and focusing shockwaves to erode tissue. This approach allows for the incorporation of rounded edges that prevent damage to eye tissue during insertion into the eye and during operation. This approach contrasts significantly with the present practice of using sharp tips and thin walls to cut away tissue by a "jack hammer" ultrasonic vibration of the tip.

In one embodiment, the wall thickness is significantly increased compared with prior art tips resulting in a greater end face or rim surface area. The rim acts as an acoustic horn, thus, increasing the surface area of the rim with directly proportionally increase the generation of micro bubbles. Instead of increasing the outer dimension of the tip (compared to existing tips) which would increase the overall size of the tip and make it more difficult to insert in the eye and maneuver during operation, it is preferred to reduce the inner diameter of the lumen of the tip to increase the surface area of the rim.

In another embodiment, the end face of the tip is provided with a concave recess designed to focus the ultrasonic acoustic waves. The surface of the concave recess can be smooth or faceted, or portions can be smooth and/or faceted. In this embodiment, the concave recess can be provided in only a portion of the end face leaving a planar rim, or almost the entire end face can be recessed leaving only the outer rounded rim.

In a further embodiment, the end face is substantially curved, preferably by a Gaussian curve. More specifically, the curved surface extends from the entrance to the lumen to the outer cylindrical surface of the distal end of the tip. Viewing a longitudinal cross section of the tip, the wall terminates at a convex surface. The convex surface ends of the tip focus the ultrasonic acoustic waves at a focal point anterior to the tip.

BRIEF DESCRIPTION OF THE DRAWINGS

FIG. 1 is a top view of an embodiment of the distal end of a phacoemulsification tip according to the present invention;

FIG. 2 is a side view of the phacoemulsification tip as shown in FIG. 1;

FIG. 3 is a partially broken away longitudinal cross-sectional view showing the details of another embodiment of a phacoemulsification tip according to the present invention;

FIG. 4 is an end view of the tip shown in FIG. 3;

FIG. 5 is a partially broken away longitudinal cross-sectional view showing the details of a further embodiment of a phacoemulsification tip according to the present invention; and FIG. 6 is an end view of the tip shown in FIG. 5.

DETAILED DESCRIPTION OF PREFERRED EMBODIMENTS

The present invention concerns the details of the structure and design of the distal ends of tips of phacoemulsification needles. Various designs of phacoemulsification tips according to the present invention are shown in FIGS. 1-6. These tips are preferably made of titanium metal to resist wear and withstand operational stresses.

A general embodiment of the present invention is shown in FIGS. 1 and 2. In these figures, details of the distal end 10 of a phacoemulsification needle tip are illustrated. The distal end 10 is defined by a cylindrical end portion of the needle tip having an inner diameter 12 and an outer diameter 14. A lumen 16 extends through and is defined by the inner surface diameter of the tip 10. The lumen is shown as having a uniform diameter, however, it is possible to have a lumen of a different shape, and/or varying diameter.

The inner diameter 12 has a dimension in the range of approximately 0.25 to 0.75 mm, preferably 0.30 to 0.70 mm, and most preferably 0.40 to 0.05 mm. These diameters generate better acoustic wave clouds with more transient microbubbles as shown by a prototype that totally erodes the cataract rather than creating an erosion only anterior to the thin rim of prior art tips with 0.91 mm lumens.

The outer diameter 14 has a dimension in the range of approximately 0.95 to 1.05 mm, preferably 0.97 to 1.03 mm, and most preferably 1.00 mm. These dimensions allow easy access to the eye interior via small incisions, and is the size surgeons have developed phaco techniques around. A change in outer diameter would require different incisions and increase risk of thermal damage if the tip were to be torqued in the incision.

The thickness 15 of the wall of the distal end 10 of the needle tip defined between the inner surface of the lumen 16 and outer surface of the distal end 10, and is in the range of approximately 0.15 to 0.35 mm, preferably 0.20 to 0.32 mm, most preferably 0.25 to 0.30 mm, and optimally 0.30 mm.

In this embodiment, an end face or rim 17 is defined at the very end of the distal end 10. Specifically, the end face surface or rim 17 extends from the entrance of the lumen 16 to the outer surface of the distal end 10.

The distal end 10 of the phacoemulsification tip is beveled at an angle 18. This angle 18 is set in the range of preferably 15° to 60°, most preferably 15° to 45°, and optimally 30°. The surgeon must be able to see the site of tip action, and be able to fixate loose pieces of cataract to the tip end before a burst of phaco energy is delivered. This is best done if the tip angle is 30°.

Further, the leading edge 20 is slightly rounded, as shown in FIG. 2, to prevent burring with potential tissue tearing. The radius of curvature of this edge is preferably 0.060 to 0.070 mm. In addition, the remaining portions of the outer edge 22 of the distal end 10 are also rounded for the same purpose.

The wide end face of this embodiments permits the generation of huge numbers (millions) of micron sized unstable bubbles that implode within a few acoustic cycles. These shock waves generate shock waves in a range of 300–500 atmospheres, and fluid waves in a range of 20 to 30 meters per second. This energy front erodes tissue in fluid anterior to the tip. The pulverized tissue is then removed along with fluid by irrigation, or by means of an aspirating pump that pulls the fluid up the lumen 16 and away form the operative area. This improved tip focuses erosion energy in front of its distal end making it more efficient.

The rounded outer edges 20, 22 prevent tissue injury and the 0.40 lumen allows this tip to be used to remove softer material by aspiration, thus obviating the need for other aspirating tips. This improved tip resists damage allowing the tip to be used many times before it needs to be replaced.

Another embodiment of a distal end 50 of a phacoemulsification tip according to the present invention is shown in FIGS. 3 and 4. The distal end 50 is provided with a focusing surface 52 to focus the ultrasonic acoustic shock waves to more efficiently produce microbubbles. In this embodiment, the focusing surface is define by a curved surface. Further, the curved surface in this embodiment is a round surface, or has a constant radius of curvature, as shown in FIG. 3.

The round focusing surface extends from the inner surface 54 of the lumen 56 to the end face 58 of the distal end 10. More specifically, the focusing surface is defined by a concave recess provided and centered in the end face 58 of the distal end 10. The apex of the concave surface opens into the lumen 56. Alternatively, the focusing surface 52 in this embodiment can be defined by a plurality of curve segments or flat facets, or combinations, which provide the same focusing effect as the curved surface illustrated in FIG. 3. For example, the focusing surface 52 can be a curved faceted concave surface instead of smoothed curved surface as illustrated.

The distal end 50 in this embodiment can be provided with a rounded leading edge 60. The remaining portions of the outer edge can also be rounded. Further, the distal end 50 is preferably beveled, however, theoretically the end face could made to be perpendicular to the tip axis, and the concave recess set off angle into the perpendicular end face. For example, the focusing surface 52 can be made off angle by drilling into the end face at an angle incident to the end face.

The size of the end face 52 can be reduced by increasing the diameter of the focusing surface. However, a sufficient rim thickness should be provided to prevent metal fatigue. Further, the curved focusing surface 52 can be Gaussian curved instead of rounded (concave) leaving a rim defined by end face 58.

The distal end is further characterized by an inner diameter 62, an outer diameter 64, a wall thickness 66, and a rim thickness 67, as shown in FIG. 4. The rim thickness 67 is preferably 0.03 to 0.10 mm, and optimally 0.03 mm. The rim thickness need not be the same throughout the circumference of the tip.

The focusing surface 52 of this embodiment provides a larger surface area for generating a greater number of transient microbubbles. This distal end can be manufactured by providing a flat beveled end to the tip by cutting, grinding and/or other known metal working techniques. The flat end face is recessed, for example, by using a ball drill.

A further embodiment of the distal end 100 of a phacoemulsification needle tip is shown in FIGS. 5 and 6. This embodiment illustrates the most advanced phase of development of distal ends according to the present invention.

In this embodiment, a focusing surface 102 is provided at the end of the distal end 100. The focusing surface 102 can be a continuous curved surface or a faceted curve surface, or combination of these surfaces. Optimally, the focusing surface 102 is defined by a Gaussian curved (normal curved) surface to maximize the focusing of the ultrasonic acoustic waves in theory. This particular embodiment can also be provided with rounded edges 104 to prevent metal burr formation and injury to eye tissue during insertion and operation.

The curved surface of the focusing surface 102 extends from the inner surface 106 of the lumen 108 to the rounded edges 104. Unlike the other embodiments illustrated, there exists no flat end face due to the continuous curved nature of the focusing surface 102. This type of curved surface is designed to generate a focal point F1 of acoustic wave energy. The shock and fluid energy front generated by this tip is expected to extend a few millimeters to theoretical focus point F2.

The distal end 100 can be furthered defined as a cylinder having an inner diameter 110, an outer diameter 112, and a rim thickness 114. The rim thickness 114 is preferably in the range of 0.030 to 0.10 mm depending upon the manufacturing technique.

The distal ends of the phacoemulsification tips according to the present invention can be manufactured by known metallurgy techniques. However, new methods of manufacture may include utilizing more stress resistant titanium alloys plus diamond honing of the interior and exterior surfaces of the tip. This honing will reduce harmonic restitution and lessen metal fatigue. Such honing will also improve dimensional tolerances thus providing better acoustic functioning, and corresponding shock wave generation.

EXAMPLE

A phaco tip was prepared with polished and rounded edges, and a 0.40 mm lumen. The end face of the tip was faceted with a smooth circular surface by application of an approximately 1.08 mm diameter round ball drill leaving a smooth edged rim of approximately 0.50 mm width.

SETTINGS FOR STORZ PREMIER PHACO

A. Initial grooves and crater made with 20% linear phaco and 80 mm Hg fixed vacuum.

B. Deep grooves made with the same settings, division of nucleus done by cross instrument cracking.

C. Loose pieces eroded with tip in center of the bag.

D. Soft peripheral cataract eroded with 5% fixed phaco power and 200 mm Hg linear vacuum.

E. Irrigation aspiration done with the same tip with 200 mm Hg vacuum and completed with split irrigation aspiration manual method using side ports at 3 and 9 to maintain optical quality of the cornea.

SETTINGS FOR ALCON 10,000 PHACO

A. Initial grooves made with 50% phaco power, softer material at near end of surgery removed with 20 to 40% power and vacuum 120 mm Hg with pump at 20 cc/min.

CLINICAL OBSERVATIONS

1. Focused phaco tip erodes hard cataract nuclei with a groove the width of the tip because energy wave is focused anterior to it with little shock energy wave directed laterally. This concentrated energy front permits erosion with only 20% maximum phaco power with the Storz Premier, and 50% with the Alcon 10,000. These are very low levels that protect the eye tissue from excess energy. The smoothed polished surface of the tip generates a better focus of acoustic waves.

2. Few air bubbles are released form bss solution presumably because the energy wave is concentrated more by the faceted face and smooth polished surfaces of the tip.

3. Use of 5% fixed phaco power with maximum 200 mm Hg vacuum allows nuclear fragments to be held by the faceted face before small amount of phaco energy is given to erode the fragment. Also, little movement of nuclear fragments (i.e. chatter) was observed with Storz Premier.

4. Focused phaco tip works well for 1A of cortex and is safer because edges are not sharp. The extra smooth polish of the tip allows greater safety when working on or near the capsule or Descemet's.

5. The smooth rounded edges reduces the risk of stripping Descemet's as the tip enters the edge via small incisions.

6. The tip shows no sign of metal damage with sharp burr formation after 80 procedures.

7. The same tip is used to aspirate soft cataract protein and even softer material in the cataract periphery (cortex). This shortens the time needed for surgery.

8. It has been noted that the tip creates a narrower groove in a hard nucleus as compared to a prior art 0.91 lumen tip, and fewer macrobubbles of air are released from the salt solution when this tip is used.

9. The amount of energy that needs to be delivered to the tip by the phaco console is less than that required if a prior art tip is used on the same device.

SUMMARY

The tested phaco tip performed as theorized. It reduces the amount of phaco energy needed to accomplish nucleus erosion, thus reducing the risk to eye tissue. It's smooth surface and edges and the faceted face deliver a better acoustic focus and protects Descemet's membrane and capsule from injury. It is believed that the recessed faceted face and absence of sharp edges protects the tip from damage during use.

I claim:

1. A phacoemulsification device, comprising:
a needle having a distal end with a lumen, said distal end belveled, and including curvature means, extending around a perimeter of said lumen at said distal end, for increasing the generation of microbubbles and focusing shockwaves to erode tissue.

2. A device according to claim 1, wherein said lumen diameter is preferably in the range of 0.30 to 0.70 millimeters, and the outer diameter of said distal end is preferably in the range of 0.97 to 1.03 millimeters.

3. A device according to claim 2, wherein said lumen diameter is most preferably in the range of 0.40 to 0.50 millimeters and said outer diameter is preferably in the range of 0.97 to 1.03 millimeters.

4. A device according to claim 3, wherein said lumen diameter is approximately 0.40 millimeters and said outer diameter is approximately 1.00 millimeters.

5. A device according to claim 1, wherein said distal end is provided with said beveled end set at an angle in the range of 15 to 60 degrees.

6. A device according to claim 5, wherein said distal end is provided with said beveled end set at an angle preferably in the range of approximately 15 to 45 degrees.

7. A device according to claim 6, wherein said beveled end is set at 30 degrees.

8. A device according to claim 5, wherein said beveled end is flat.

9. A device according to claim 5, wherein a portion of said beveled end is flat.

10. A device according to claim 9, wherein said distal end is provided with an outer edge that is at least partially rounded.

11. A device according to claim 9, wherein said beveled end is provided with a recess.

12. A device according to claim 11, wherein said recess is defined by a curved surface.

13. A device according to claim 12, wherein said curved surface is a continuous curved surface.

14. A device according to claim 12, wherein said curved surface is a faceted curved surface.

15. A device according to claim 12, wherein said recess surface is a concave surface.

16. A device according to claim 1, wherein an end face of said distal end is provided with a recess defining said curvature means.

17. A device according to claim 16, wherein said distal end is provided with said recess.

18. A device according to claim 16, wherein said recess is defined by a curved surface.

19. A device according to claim 18, wherein said curved surface is a Gaussian curved surface.

20. A device according to claim 19, wherein said distal end is provided with said recess in said beveled end.

21. A device according to claim 18, wherein said curved surface is a continuous curved surface.

22. A device according to claim 21, wherein said curved surface is a Gaussian curved surface.

23. A device according to claim 18, wherein said curved surface is a faceted curved surface.

24. A device according to claim 16, wherein said recess is defined by a concave surface.

25. A device according to claim 1, where said lumen is centered in the distal end.

26. A device according to claim 1, wherein said distal end is configured to focus shock waves generated by microbubbles formed at said distal end substantially towards one or more specific focal points.

27. A device according to claim 1, wherein said lumen has a diameter in the range of approximately 0.25 to 0.75 millimeters, and said distal end an outer diameter in the range of approximately 0.95 to 1.05 millimeters.

28. A phacoemulsification device, comprising:
a needle having a distal end beveled end with a lumen, said distal end including microbubble generation means for increasing the generation of microbubbles and curvature means, extending around a perimeter of said lumen at said distal end, for focusing shockwaves generated from said distal end to enhance the erosion of tissue.

29. A device according to claim 28, wherein said microbubble generation means is defined by a substantially wide end face.

30. A device according to claim 28, wherein said microbubble generation means is at least partially defined by a focusing surface that focuses shockwaves generated by microbubbles generated from said distal end during operation.

31. A device according to claim 30, wherein said focusing surface is provided substantially as an end face of said distal end.

32. A device according to claim 31, wherein said focusing surface is defined between said lumen and an outer surface of said distal end.

33. A device according to claim 32, wherein at least a portion of said focusing surface is a continuous curved surface.

34. A device according to claim 33, wherein at least a portion of said focusing surface is a faceted curved surface.

35. A device according to claim 32, wherein at least a portion of said focusing surface is a faceted curved surface.

36. A device according to claim 32, wherein said curved surface is a rounded surface.

37. A device according to claim 32, wherein said curved surface is a Gaussian curved surface.

38. A device according to claim 30, wherein said focusing surface is defined by a flat end face having rounded edges.

39. A device according to claim 30, wherein said focusing surface is defined by said beveled end, said beveled end further comprising a flat end face having rounded edges and a recess in the beveled flat end face.

40. A device according to claim 30, wherein said focusing surface is defined by the beveled end, said beveled end further having rounded edges, and a continuous curve extending from said lumen to said rounded edges.

41. A device according to claim 40, wherein said continuous curved surface is a Gaussian curved surface.

* * * * *